United States Patent
Sato et al.

(10) Patent No.: US 10,797,393 B2
(45) Date of Patent: Oct. 6, 2020

(54) READING DEVICE ANTENNA

(71) Applicants: KYOTO UNIVERSITY, Kyoto-shi, Kyoto (JP); HOGY MEDICAL CO., LTD., Tokyo (JP); WELCAT INC., Tokyo (JP)

(72) Inventors: Toshihiko Sato, Kyoto (JP); Yojiro Yutaka, Kyoto (JP); Koichi Matsushita, Tokyo (JP); Jiro Kato, Tokyo (JP); Kaoru Nayuki, Tokyo (JP)

(73) Assignees: KYOTO UNIVERSITY, Kyotos-shi, Kyoto (JP); HOGY MEDICAL CO., LTD., Minato-ku, Tokyo (JP); IDEC AUTO-ID SOLUTIONS CORPORATION, Osaka-shi, Osaka (JP)

( * ) Notice: Subject to any disclaimer, the term of this patent is extended or adjusted under 35 U.S.C. 154(b) by 0 days.

(21) Appl. No.: 16/333,705

(22) PCT Filed: Sep. 8, 2017

(86) PCT No.: PCT/JP2017/032404
§ 371 (c)(1),
(2) Date: Mar. 15, 2019

(87) PCT Pub. No.: WO2018/051901
PCT Pub. Date: Mar. 22, 2018

(65) Prior Publication Data
US 2019/0229420 A1    Jul. 25, 2019

(30) Foreign Application Priority Data
Sep. 16, 2016   (JP) ................................ 2016-181789

(51) Int. Cl.
*H01Q 1/22*   (2006.01)
*H01Q 7/08*   (2006.01)
(Continued)

(52) U.S. Cl.
CPC ............... *H01Q 7/08* (2013.01); *A61B 5/002* (2013.01); *A61B 5/06* (2013.01); *A61B 90/39* (2016.02);
(Continued)

(58) Field of Classification Search
CPC ........ H01Q 1/273; H01Q 1/2216; H01Q 7/08; H01Q 1/526; H01Q 1/2208; H01Q 1/521;
(Continued)

(56) References Cited

U.S. PATENT DOCUMENTS 8,634,931 B2 *   1/2014   Min ......................... A61N 1/05
                                                            607/115
9,013,170 B2 *   4/2015   Yamaguchi ........ G01R 29/0842
                                                            174/117 F (Continued)

FOREIGN PATENT DOCUMENTS

JP         2010-284 A      1/2010

OTHER PUBLICATIONS

International Search Report for PCT/JP2017/032404 dated Nov. 21, 2017 [PCT/ISA/210].

*Primary Examiner* — Haissa Philogene
(74) *Attorney, Agent, or Firm* — Sughrue Mion, PLLC

(57) ABSTRACT

An IC tag reading device is provided that has increased directivity and is capable of determining an accurate position of an IC tag inserted into and placed in a human body even when the operation range of the antenna of the reading device is limited, such as in thoracoscopy, without causing reduction in detectable distance. A reading device antenna for reading an IC tag that has been inserted into a human body and placed at a certain position in order to locate a lesion includes a coil portion having a coil with a predetermined number of turns in a circumferential direction, and a shield portion that covers at least an approximately half of
(Continued)

the coil portion in the circumferential direction and causes a bias in a magnetic flux generated from the coil.

7 Claims, 3 Drawing Sheets

(51) Int. Cl.
*A61B 90/00* (2016.01)
*A61B 5/06* (2006.01)
*H01Q 1/27* (2006.01)
*A61B 5/00* (2006.01)
*H01Q 1/52* (2006.01)

(52) U.S. Cl.
CPC ......... *H01Q 1/2208* (2013.01); *H01Q 1/2216* (2013.01); *H01Q 1/273* (2013.01); *H01Q 1/521* (2013.01); *H01Q 1/526* (2013.01); *A61B 2090/397* (2016.02)

(58) Field of Classification Search
CPC ........ H01Q 1/2225; A61B 5/06; A61B 90/39; A61B 5/002; A61B 2090/397; A61B 5/062; A61B 2505/05
See application file for complete search history.

(56) References Cited

U.S. PATENT DOCUMENTS 9,672,460 B2 * 6/2017 Hoffa .................. B23K 5/00
9,945,645 B2 * 4/2018 Yamauchi ............ B60R 21/264

\* cited by examiner

FIG.1
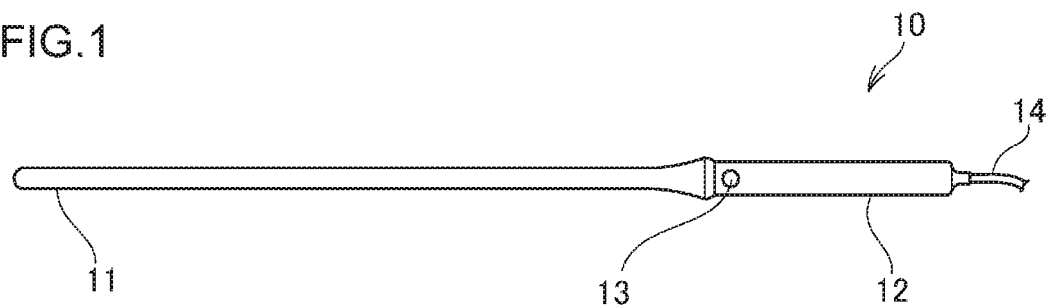
FIG.2
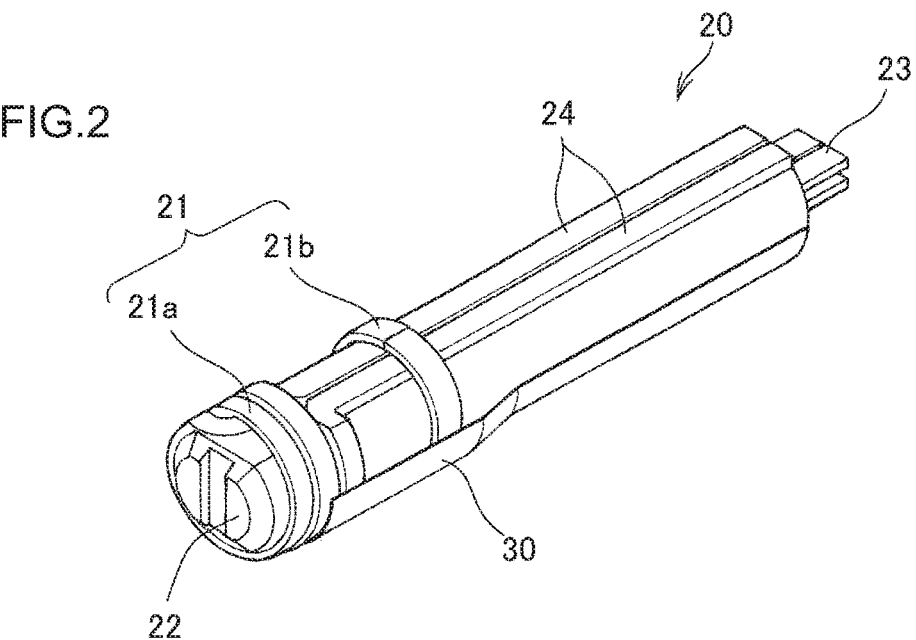
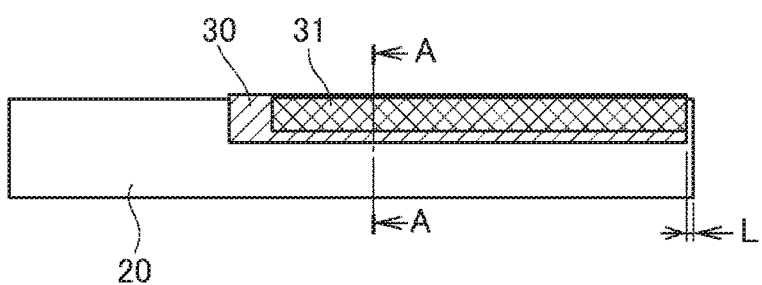
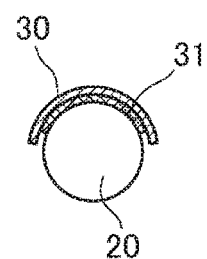
FIG.3(a)　　　　　　　　FIG.3(b)

Y-direction [mm]

X-direction [mm]

READING DEVICE ANTENNA

CROSS REFERENCE TO RELATED APPLICATIONS

This application is a National Stage of International Application No. PCT/JP2017/032404, filed on Sep. 8, 2017, which claims priority from Japanese Patent Application No. 2016-181789, filed on Sep. 16, 2016.

TECHNICAL FIELD

The present invention relates to an antenna for an IC tag reading device, and more particularly, to a reading device antenna that can accurately ascertain the position of a lesion in a human body by receiving a signal transmitted from an IC tag that has been inserted and placed at the lesion.

BACKGROUND ART

An extirpative surgery is usually performed while simultaneously checking the position of a lesion to be removed which was confirmed with image diagnostic equipment such as an endoscope or CT prior to the surgery.

Various methods are known for such a surgery, including one that involves inserting an IC tag into a human body and placing it at a certain position, bringing the antenna of a reading device having the antenna and a reader close to the IC tag so as to read the position of the placed IC tag with the reader and check it, and then extirpating the lesion, as described in Patent Literature 1, for instance.

With this kind of surgery method, a lesion can be easily located by reading an IC tag during the surgery even in a case where the lesion is difficult to locate, e.g., due to shrinkage of a lung in an extirpation with a thoracoscope when a lung cancer is to be extirpated.

CITATION LIST

Patent Literature

Patent Literature 1: Japanese Patent Laid-Open No. 2010-284

SUMMARY OF INVENTION

Technical Problem

However, since a conventional IC tag reading device uses a loop antenna for its antenna, the device is configured such that a magnetic flux is uniformly formed around the antenna of the reading device. As a result, a detection range 160 of the device becomes wide as shown in FIG. 7, which leads to the problem of difficulty in determining the relative position of an IC tag 140 to a reading device antenna 100.

Also, in thoracoscopy for example, the reading device antenna 100 is moved at a chest wall 161 as a fulcrum, so that the positional relationship between a lesion with the IC tag 140 attached thereon and the reading device antenna 100 is limited and the lesion cannot be approached at a desired angle. This presents the problem of further complication in determining the position of the IC tag 140, along with the fact that the detection range 160 of the reading device antenna 100 is wide.

Furthermore, for a safety reason associated with sterilization, tools for use in determination of a lesion with an endoscope such as in thoracoscopy are preferably single-use (disposable); however, making tools disposable leads to the problem of difficulty in keeping costs low.

The present invention has therefore been made to solve these problems and an object thereof is to provide an antenna for an IC tag reading device which is capable of determining an accurate position of an IC tag inserted into and placed in a human body even when the operation range of the reading is limited, e.g., in thoracoscopy, and which is also inexpensive and disposable.

Solution to Problem

For attaining the object, a reading device antenna according to the present invention is a reading device antenna for reading an IC tag that has been inserted into a human body and placed at a certain position in order to locate a lesion, the reading device antenna including: a coil portion having a coil with a predetermined number of turns in a circumferential direction; and a shield portion that covers at least an approximately half of the coil portion in the circumferential direction and causes a bias in a magnetic flux generated from the coil.

Also, in the reading device antenna according to the present invention, the coil portion preferably has a ferrite core inserted therein along an axial direction.

Also, in the reading device antenna according to the present invention, the coil preferably includes at least two or more coil components, with the coil components being positioned apart from each other in the axial direction and being coupled to each other by a magnetic field.

Also, in the reading device antenna according to the present invention, the shield portion is preferably attached at a predetermined spacing from a tip of the coil portion in the axial direction.

Also, the reading device antenna according to the present invention preferably include a magnetic sheet between the shield portion and the coil portion.

Further, in the reading device antenna according to the present invention, the magnetic sheet preferably contains iron oxide.

Moreover, the reading device antenna according to the present invention preferably includes a trigger switch.

Advantageous Effects of Invention

The present invention includes a shield portion that covers at least an approximately half of the coil portion in the circumferential direction and causes a bias in a magnetic flux generated from the coil. Thus, the sensitivity at the position of the shield portion is weakened and a uniform magnetic flux is not formed such that an area where no detection is performed is created. This enables accurate determination of the position of an IC tag even in a case with a limited range of movement of the reading device, such as in thoracoscopy. Additionally, the antenna according to the present invention can be constructed by attachment of the shield portion without requiring mounting of a separate notch filter or the like, and thus can be manufactured at reduced cost.

BRIEF DESCRIPTION OF DRAWINGS

FIG. 1 is a top view of a reading device antenna according to an embodiment of the present invention.

FIG. 2 is a perspective view for describing the structure of a coil portion of the reading device antenna according to the embodiment of the present invention.

FIG. 3(*a*) is a side view of the coil portion of the reading device antenna according to the embodiment of the present invention and FIG. 3(*b*) is a cross-sectional view taken at A-A in FIG. 3(*a*).

DESCRIPTION OF EMBODIMENT

The reading device antenna according to the present invention is described below with reference to the drawings. Note that the embodiment described below is not intended to limit the subject matters set forth in the claims and not all of the combinations of features described in the embodiment are essential for the solution of the present invention.

Figure 4:
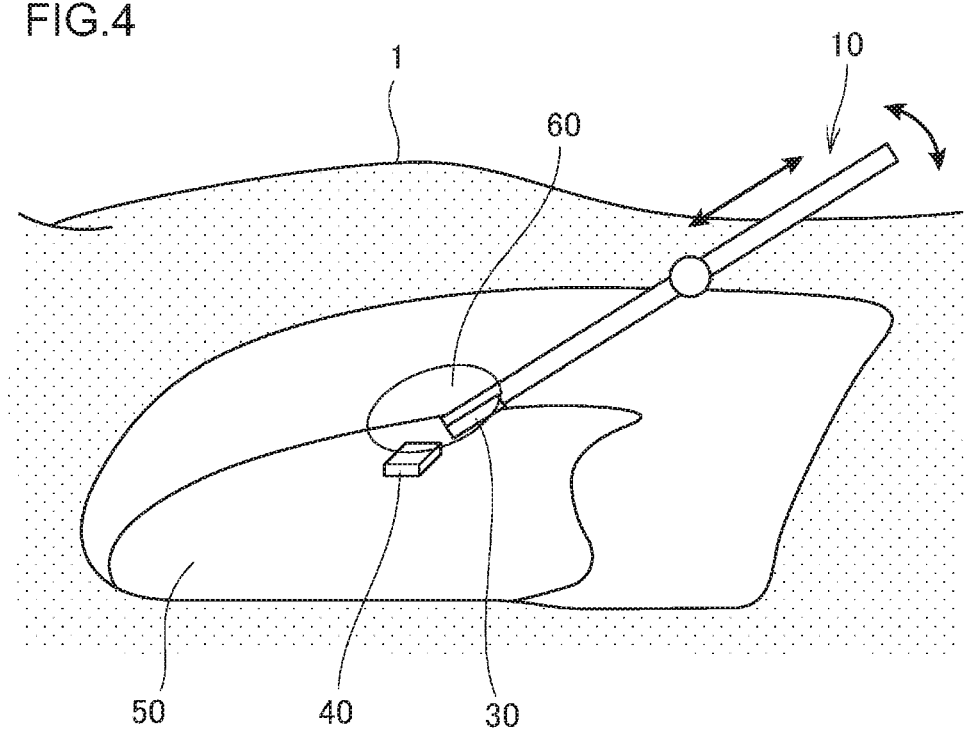
FIG. 4 illustrates how the reading device antenna according to the embodiment of the present invention is used.

FIG. 1 is a top view of a reading device antenna according to an embodiment of the present invention; FIG. 2 is a perspective view for describing the structure of a coil portion of the reading device antenna according to the embodiment of the present invention; FIG. 3(*a*) is a side view of the coil portion of the reading device antenna according to the embodiment of the present invention and FIG. 3(*b*) is a cross-sectional view taken at A-A in FIG. 3(*a*); and FIG. 4 illustrates how the reading device antenna according to the embodiment of the present invention is used.

As shown in FIG. 1, a reading device antenna 10 according to the embodiment is a rod-shaped component and contains a coil portion 20, described later, in a leading end portion 11. On its basal-end side, the reading device antenna 10 includes a grip portion 12 and a trigger switch 13 positioned adjacent the grip portion 12. The trigger switch 13 is capable of switching on and off of reading and is configured to be able to start reading by being operated when reading is required. The reading device antenna 10 thus configured can read an IC tag that has been inserted through the chest wall or the like of a human body and placed at a certain position for locating a lesion. In doing so, the relative distance to the IC tag is adjusted by moving the reading device antenna 10 at the chest wall as a fulcrum by gripping the grip portion 12.

The grip portion 12 also has a wiring 14 attached thereon such that the coil portion 20 contained in the leading end portion 11 detects a signal received from the IC tag and sends the detected signal to a reader (not shown) via the wiring 14. The reading device has the antenna 10 and the reader.

Now turning to FIG. 2, the coil portion 20 contained in the leading end portion 11 is described. The coil portion 20 has a coil 21 with a predetermined number of turns in the circumferential direction and a ferrite core 22 inserted along the axial direction of the coil.

The coil 21 includes a first coil 21*a* located on the leading-end side and a second coil 21*b* positioned apart from and at a predetermined spacing from the first coil 21*a*. The first coil 21*a* and the second coil 21*b* are positioned such that they are coupled to each other by a magnetic field and are in communication with a connection terminal 23, connected with the wiring 14, via a connecting portion 24 extending along the axial direction of the ferrite core 22. The first coil 21*a*, the second coil 21*b*, and the connecting portion 24 are each preferably a flat rectangular enameled wire and the like.

The coil portion 20 has attached thereon a shield portion 30 that covers at least an approximately half of the coil portion 20 in the circumferential direction. The shield portion 30 is composed of a nonmagnetic component such as aluminum tape, causing a bias in a magnetic flux generated from the coil 21.

Also, as shown in FIG. 3(*a*), the shield portion 30 is attached at a predetermined spacing L from the tip of the coil portion 20 in the axial direction, specifically, is attached at a spacing of about 1.0 to 5.0 mm. Due to such attachment of the shield portion 30 at the predetermined spacing from the tip, the detection range on the leading-end side of the reading device antenna 10 is configured such that no bias is caused in it by the shield portion 30.

Further, a magnetic sheet 31 is present between the shield portion 30 and the coil portion 20. The magnetic sheet 31 is a magnetic material containing iron oxide and prevents reduction in inductance. As shown in FIG. 3(*b*), the magnetic sheet 31 is covered by the shield portion 30, with the magnetic sheet 31 being positioned so as not to stick out of the shield portion 30. Without attachment of the magnetic sheet 31, reduction in inductance would be large and hence change in a tuning constant would be large, but it is also possible to omit the magnetic sheet 31 by regulating the tuning constant beforehand.

When the reading device antenna 10 configured as described above is inserted into a human body 1, a bias occurs in a detection range 60 generated by the coil portion 20 in such a manner that the detection range 60 on the leading-end side is secured, while the detection range 60 is not formed on the side of the shield portion 30 and hence the sensitivity on the side of the shield portion 30 is decreased. Accordingly, the position of the IC tag 40 is determined from the detection range 60 on the leading-end side by positioning the antenna such that the shield portion 30 is oriented toward an organ 50 with a lesion to prevent detection from taking place on the organ 50 side. This can allow easy and accurate determination of the position of the IC tag 40 through an intuitive operation.

When the shield portion 30 is oriented toward the opposite side of the organ 50, the position of the IC tag can be detected in a wide detection range as in the conventional method, so a rough position of the IC tag 40 can be assessed.

Next, a result of comparison between the reading device antenna 10 of this embodiment and a conventional reading device antenna 100 without the shield portion 30 is described.

Figure 5:
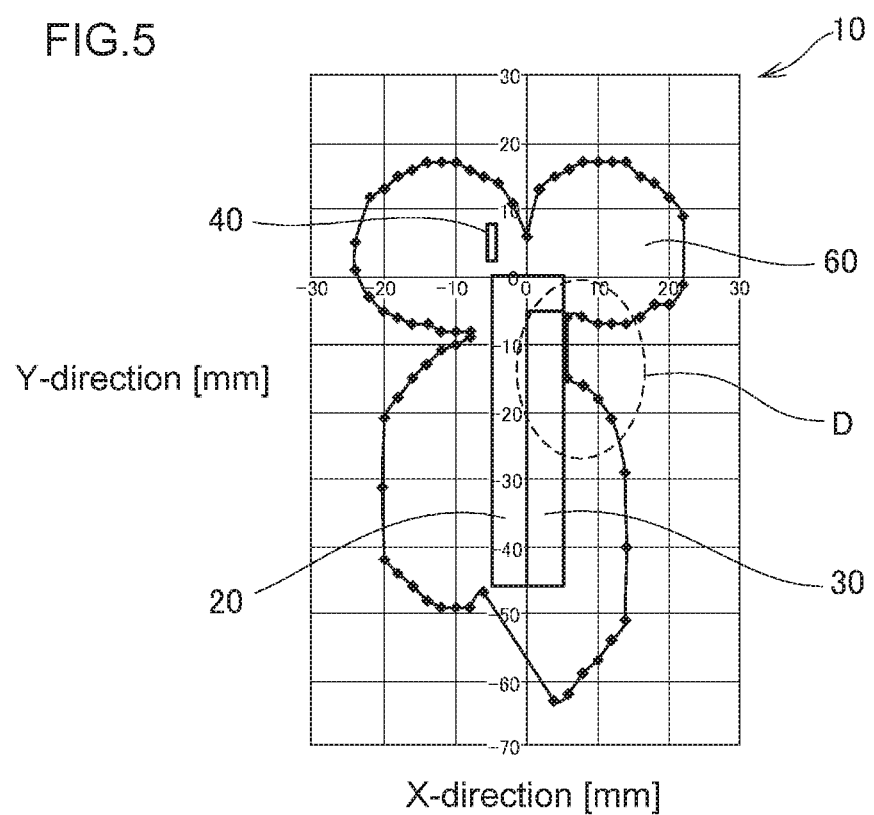
FIG. 5 shows the reading range of the reading device antenna according to the embodiment of the present invention.
Figure 6:
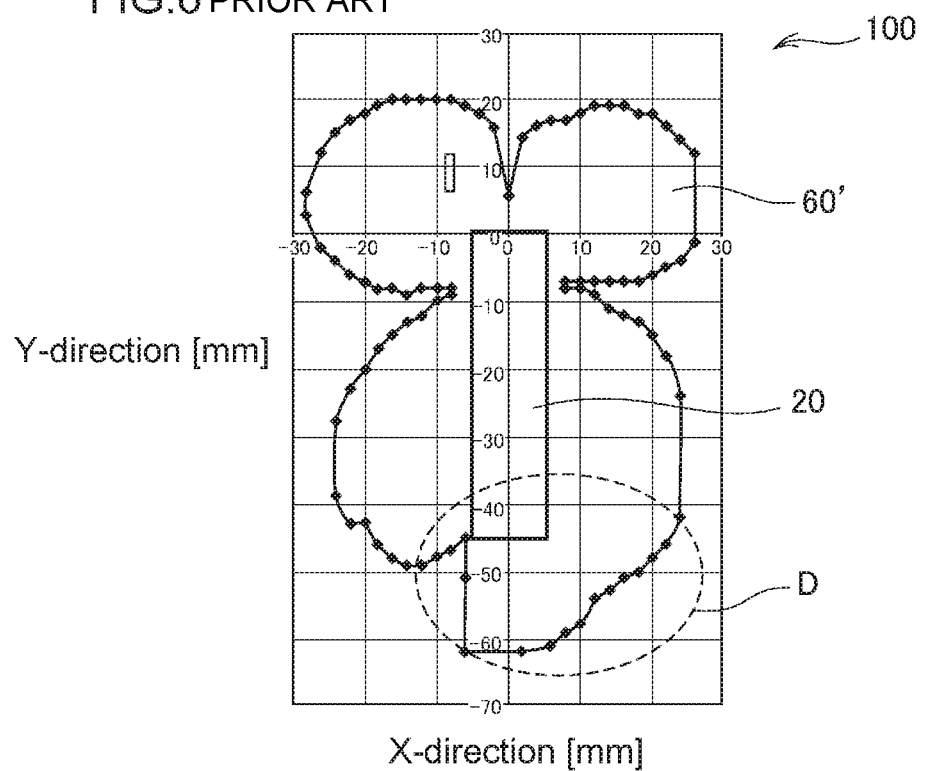
FIG. 6 shows the reading range of a conventional reading device antenna.
Figure 7:
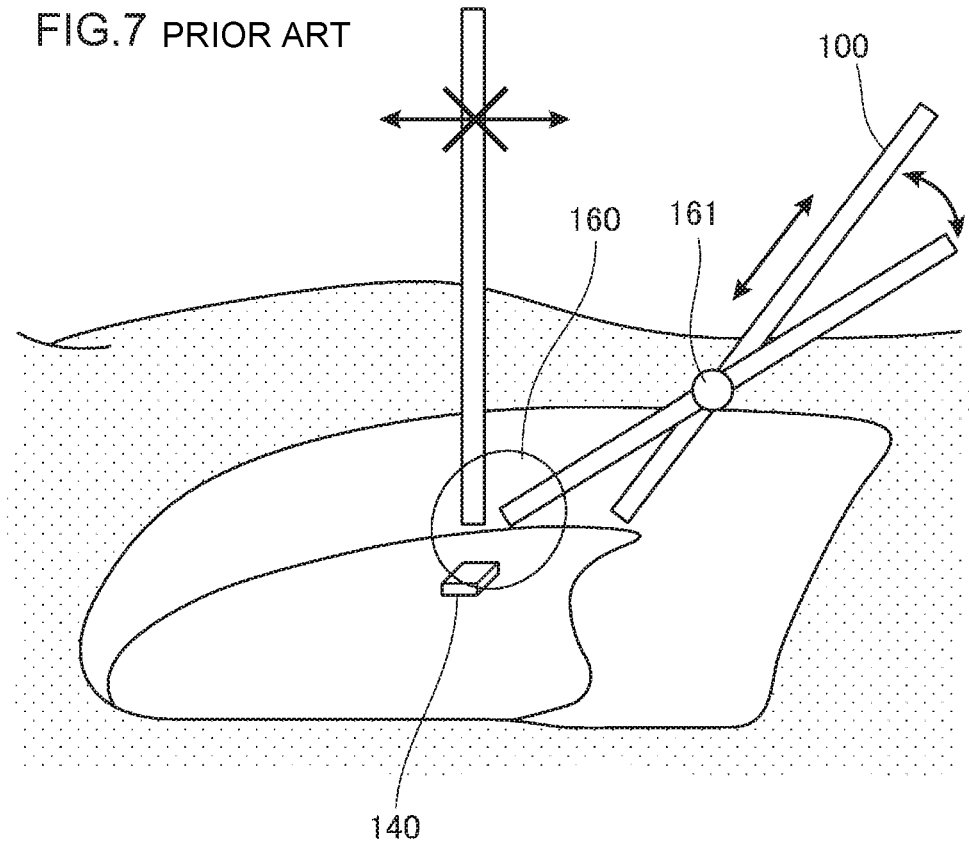
FIG. 7 illustrates how the conventional reading device antenna is used.

FIG. 5 shows the reading range of the reading device antenna according to the embodiment of the present invention, and FIG. 6 shows the reading range of the conventional reading device antenna.

As shown in FIG. 5, a bias D has occurred in the detection range 60 on the side of the shield portion 30 because of the shield portion 30 provided on the coil portion 20 of the reading device antenna 10 according to this embodiment. On the leading-end side, it can be seen that the detection range 60 is sufficiently formed because the shield portion 30 is attached at the predetermined spacing.

Therefore, when the IC tag 40 is present in the detection range 60 on the leading-end side, the position of the IC tag 40 can be detected with high accuracy. Additionally, since the detection range on the leading-end side can be used as an effective detection range by orienting the shield portion 30 toward the organ side, when the IC tag 40 has been detected, it can be known that the IC tag is present on the leading-end side of the coil portion 20. Accordingly, the position of the IC tag 40 can be determined without having a complicated mechanism such as a functional unit in the antenna itself even in a case with a limited range of movement of the coil portion 20, such as in thoracoscopy.

In contrast, the reading range of the conventional reading device antenna 100 is as shown in FIG. 6, where the bias D as shown in FIG. 5 is not formed and a detection range 60' is uniformly formed both on the leading-end side and lateral side of the coil portion 20. Under this condition, when the IC tag 40 is present in the detection range 60', the position of the IC tag 40 relative to the coil portion is difficult to determine because the detection range 60' is formed uniformly around the coil portion.

While the reading device antenna 10 according to the above embodiment was described for a case of using one IC tag 40, two or more IC tags may be provided and the number of IC tags may be increased or reduced as appropriate depending on the processing capability of the reader used and/or the number of IC tags that can be read. It will be apparent from the description of Claims that other modifications or improvements may be covered by the technical scope of the present invention.

REFERENCE SIGNS LIST

10, 100 . . . reading device antenna
11 . . . leading end portion
12 . . . grip portion
14 . . . wiring
20 . . . coil portion
21 . . . coil
21*a* . . . first coil
21*b* . . . second coil
22 . . . ferrite core
30 . . . shield portion
31 . . . magnetic sheet
40, 140 . . . IC tag
60, 160 . . . detection range

The invention claimed is:

1. A reading device antenna for reading an IC tag that has been inserted into a human body and placed at a certain position in order to locate a lesion, the reading device antenna comprising:
   a coil portion having a coil with a predetermined number of turns in a circumferential direction; and
   a shield portion that covers at least an approximately half of the coil portion in the circumferential direction and causes a bias in a magnetic flux generated from the coil.

2. The reading device antenna according to claim 1, wherein the coil portion has a ferrite core inserted therein along an axial direction.

3. The reading device antenna according to claim 1, wherein the coil comprises at least two or more coil components, with the coil components being positioned apart from each other in the axial direction and being coupled to each other by a magnetic field.

4. The reading device antenna according to claim 1, wherein the shield portion is attached at a predetermined spacing from a tip of the coil portion in the axial direction.

5. The reading device antenna according to claim 1, comprising a magnetic sheet between the shield portion and the coil portion.

6. The reading device antenna according to claim 5, wherein the magnetic sheet contains iron oxide.

7. The reading device antenna according to claim 1, comprising a trigger switch.

* * * * *